United States Patent

Himmele et al.

[11] Patent Number: 4,487,965
[45] Date of Patent: Dec. 11, 1984

[54] TRANS-3-(4'-TERT.-BUTYLCYCLOHEX-1'YL)-2-METHYL-1-DIALKYLAMINOPROPANES, THEIR PREPARATION AND THEIR USE AS DRUGS

[75] Inventors: Walter Himmele, Walldorf; Wolfgang Heberle, Starnberg; Friedrich-Wilhelm Kohlmann, Moorrege; Walter Wesenberg, Bujendorf ueber Eutin, all of Fed. Rep. of Germany

[73] Assignee: BASF Aktiengesellschaft, Fed. Rep. of Germany

[21] Appl. No.: 508,143

[22] Filed: Jun. 27, 1983

[30] Foreign Application Priority Data

Jul. 10, 1982 [DE] Fed. Rep. of Germany ....... 3225879

[51] Int. Cl.³ .................. C07C 85/24; C07C 87/36
[52] U.S. Cl. .................... 564/454; 564/450; 424/325
[58] Field of Search ............ 564/450, 454; 424/325

[56] References Cited

U.S. PATENT DOCUMENTS

| | | | |
|---|---|---|---|
| 2,656,385 | 10/1953 | Hogg et al. | 564/454 X |
| 2,656,386 | 10/1953 | Hogg et al. | 564/454 X |
| 3,376,341 | 4/1968 | Bauer | 564/450 |
| 3,988,373 | 10/1976 | Nakanishi et al. | 564/454 X |
| 4,078,066 | 3/1978 | Hauck et al. | 564/454 X |
| 4,161,492 | 7/1979 | Weissel | 564/450 X |
| 4,384,142 | 5/1983 | Merten et al. | 564/450 |

FOREIGN PATENT DOCUMENTS

| | | | |
|---|---|---|---|
| 2752135 | 5/1978 | Fed. Rep. of Germany | 564/454 |
| 2921221 | 12/1980 | Fed. Rep. of Germany | 564/454 |
| 237879 | 9/1945 | Switzerland | 564/454 |

Primary Examiner—Paul F. Shaver
Attorney, Agent, or Firm—Keil & Weinkauf

[57] ABSTRACT

Trans-3-(4'-tert.-Butylcyclohex-1'-yl)-2-methyl-1-dialkylaminopropanes of the formula I

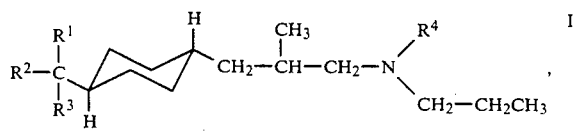

where $R^1$ and $R^2$ are each alkyl and the sum of the carbon atoms in $R^1$ and $R^2$ is 5, 6, or 7, and their salts with physiologically tolerated acids, and their preparation, are described. The novel compounds are useful as active compounds for drugs.

5 Claims, No Drawings

TRANS-3-(4'-TERT.-BUTYLCYCLOHEX-1'YL)-2-METHYL-1-DIALKYLAMINOPROPANES, THEIR PREPARATION AND THEIR USE AS DRUGS

The present invention relates to novel trans-3-(4'-tert.-butylcyclohex-1'-yl)-2-methyl-1-dialkylaminopropanes, a process for their preparation and their use in treating disorders.

It has been disclosed that 3-(4'-tert.-butylcyclohex-1'-yl)-2-methyl-1-(2',6'-dimethylmorpholino)propane and its salts can be used for controlling phytopathogenic fungi and yeasts and fungi which are pathogenic to humans (German Laid-Open Application DOS No. 2,752,135). German Laid-Open Application DOS No. 2,921,221 discloses that particularly active isomers of these compounds are those in which the substituents occupy the bis-equatorial position on the cyclohexane ring. The bis-equatorial compounds are isolated from the stereo-isomer mixtures by concentration by means of fractional distillation followed by conversion to a salt and recrystallization of the latter. This separation is very difficult and expensive. For example, the distillation has to be carried out at a temperature at which, particularly in metal vessels, partial isomerization of the morpholine radical occurs, resulting in a reduction in the activity of the substance.

We have found compounds which likewise possess antimycotic activity but are easier to prepare.

The present invention relates to trans-3-(4'-tert.-butylcyclohex-1'-yl)-2-methyl-1-dialkylaminopropanes of the formula I

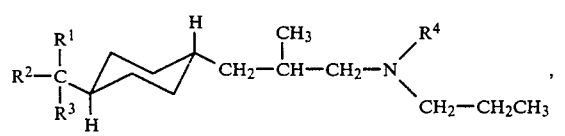

where $R^1$, $R^2$ and $R^3$ are identical or different and are each $C_1$-$C_4$-alkyl, or two of the radicals $R^1$, $R^2$ and $R^3$ together can form a cyclopentyl or cyclohexyl radical, and $R^4$ is ethyl or n-propyl, and to their salts with physiologically tolerated acids.

In the trans compounds, the substituents on the cyclohexyl ring are in the equatorial position.

$R^1$, $R^2$ and $R^3$ are each, in particular, methyl, and $R^4$ is preferably n-propyl. Examples of physiologically tolerated acids are organic carboxylic acids or inorganic acids, eg. nitric acid, hydrochloric acid, sulfuric acid, phosphoric acid, acetic acid, propionic acid, lactic acid, succinic acid, tartaric acid, citric acid, benzoic acid, salicylic acid or nicotinic acid. Preferred acids, however, are the above inorganic acids, in particular hydrochloric acid.

The novel compounds are prepared by a process wherein a compound of the formula II

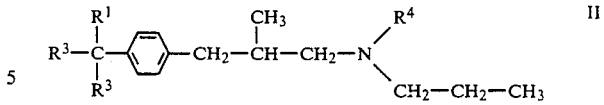

where $R^1$, $R^2$, $R^3$ and $R^4$ have the above meanings, is hydrogenated, the resulting isomer mixture is separated into the isomers, and, if required, the compound obtained is converted to its salts with physiologically tolerated acids.

The compounds II are most advantageously hydrogenated at 20°–200° C. and under a hydrogen pressure of 1–300 bar. Particularly suitable catalysts are ruthenium and palladium. Hydrogenation is advantageously carried out in a solvent, such as dioxane, isopropanol or glacial acetic acid. It is advisable to monitor the absorption of hydrogen by means of proton resonance spectroscopy. When absorption of hydrogen is complete, the reaction mixture is fractionally distilled over a column possessing about 40–70 theoretical separation stages, at 10–40 mbar and with a reflux ratio of from 1:1 to 1:20. The distillation gives the desired product in a purity (above 98.5%) which permits it to be used directly for the preparation of the pharmaceutical formulations. The novel compounds in which the substituents on the cyclohexyl ring are in the bis-equatorial position boil at a higher temperature than those in which the substituents are in the equatorial-axial position.

The novel compounds are hence substantially simpler to prepare than those mentioned in German Laid-Open Application DOS No. 2,921,221. The distillative separation does not have to be carried out under such greatly reduced pressure, and smaller apparatuses can therefore be used. The distillation gives sharp separation of the isomers, and only small intermediate fractions are obtained. Moreover, the distillation can be carried out more rapidly.

The novel compounds and their salts possess powerful antimycotic actions and a broad antimycotic spectrum of action, in particular against dermatophytes, eg. species of the genera Epidermophyton, Microsporum and Trichophyton, and yeasts, eg. species of the genus Candida. This list is not intended to restrict the microorganisms which can be controlled, but is intended only to serve as an example.

The action against dermatophytes can be demonstrated by a method as described by, for example, P. Klein in Bakteriologische Grundlagen der chemotherapeutischen Laboratoriumspraxis, Springer-Verlag Berlin, Göttingen, Heidelberg, 1957. The surprising action against yeasts was demonstrated in the pseudomycelium and mycelium phase test with *Candida albicans*. The in vitro antimicrobial activity against microorganisms was determined in the agar dilution test (P. Klein, loc. cit.).

The results are shown in Table 1.

Similar results are obtained with many other strains of the species listed in Table 1 and with strains of the species *Mikrosporon audouinii*, *Mikrosporon canis*, *Mikrosporon gypseum*, *Trichophyton violaceum*, *Trichophyton rubrum* and *Trichophyton quinckeanum*.

TABLE 1

| Substance from Example | Minimum inhibitory concentrations | | | |
|---|---|---|---|---|
| | Trichophyton mentagroph. ATCC 4807 | Candida albicans ATCC 14052 | Epidermophyton floccosum ATCC 10227 | Mikrosporon ferrugineum CBS 317.31 |
| 1 | <0.125 | <0.125 | <0.125 | <0.125 |
| 2 | 0.25 | 1 | 0.25 | <0.125 |

Furthermore, the novel compounds were tested in the guinea pig trichophyt is model (*Trichophyton mentagrophytes;* cf. Heffter-Heubner: Handbuch der experimentellen Pharmakologie, Volume XVI/11A, Springer Verlag, Berlin, Heidelberg, New York, 1967), in which the compounds were applied externally in the form of 0.2, 0.5 and 1% strength suspensions. Application was effected once daily for 4 and 7 days respectively. After the 4th and 7th day of treatment, and 7 days after the last treatment, hairs or scales were pulled off at from 3 to 5 points in the infected area in each animal, and were incubated in Sabourand dextrose bouillon.

Evaluation was carried out by monitoring fungal growth after incubation for 8 days.

Table 2 shows the fraction of animals in which infection was observed during and after treatment.

TABLE 2

| Substance | | 4 days | 7 days | 7 days after treatment |
|---|---|---|---|---|
| Example 1 | 0.2% | 3/5 | 2/5 | 1/5 |
| " | 0.5% | 0/5 | 0/5 | 0/5 |
| " | 1.0% | 1/5 | 0/5 | 0/5 |
| Clotrimazole | 0.2% | 3/5 | 3/5 | 3/5 |
| Clotrimazole | 1.0% | 2/5 | 0/5 | 3/5 |
| Tolnaftate | 1.0% | 0/9 | 0/9 | 2/9 |
| Control | — | 5/5 | 5/5 | 5/5 |

Table 2 shows that the novel substances are superior to the comparative substances.

Accordingly, the novel substances are particularly suitable for treating dermatomycoses, dermatophytoses and systemmycoses, particularly when caused by species of the genera Epidermophyton, Microsporum and Trichophyton, and yeasts, eg. species of the genus Candida.

The novel compounds can be used in the conventional pharmaceutical forms for administration, such as solutions, powders, ointments, creams or sprays. These are produced in a conventional manner, and to do this the active compounds can be mixed with the conventional pharmaceutical auxiliaries (cf. H. Sucker et al., Pharmazeutische Technologie, Thieme-Verlag, Stuttgart, 1978).

As a rule, the active compounds are applied externally in an amount of about 0.07–0.1 g/cm² of body surface every 24 hours, if appropriate in the form of several single doses. However, it is also possible to deviate from the stated doses, and to do this as a function of the nature and severity of the disorder. The optimum dose in a particular case and the frequency of administration can be determined by the doctor responsible, on the basis of his knowledge.

As a rule, the individual doses are applied once or twice daily. When used for external, local application, the formulations contain from 0.2 to 1.0, preferably 0.5, % by weight of active compound.

EXAMPLE 1

A. Preparation of the starting material 401 g of 98% strength formic acid were added to 1,428 g of 3-(4'-tert.-butylphenyl)-2-methylpropanal and 707 g of di-n-propylamine in the course of 19 hours, while stirring, so that no pronounced foam formation occurred. The $CO_2$ formed escaped via a reflux condenser. The resulting reaction mixture was subjected to a short-path distillation and 1,950 g of distillate passed over at 110°–180° C./0.6 mbar. This was fractionally distilled over a column. The fraction which passed over under 0.4 mbar and below 136° C. consisted of 97% strength 3-(4'-tert.-butylphenyl)-2-methyl-1-di-n-propylaminopropane. The yield was 1,890 g.

B. Preparation and isolation of the end product (a) 1,050 g of the product obtained as described in A, in 2,000 ml of isopropanol, were hydrogenated in an autoclave at 100°–140° C. and under a hydrogen pressure of 100–140 bar. 1 g of ruthenium oxide hydrate was used as a catalyst. After 44 hours, the product was stirred with 25 g of active carbon, and the mixture was then filtered. The filtrate was evaporated down and then subjected to a short-path distillation.

The product (1,020 g) which passed over at 125°–135° C./0.6 mbar was fractionally distilled over a column.

(b) The product which was obtained as described in (a) and consisted of 56.2% of cis- and 43.8% of trans-1,4-cyclohexane derivative was fractionated under a pressure of 37 bar, in a column which had a height of 160 cm and a diameter of 2.9 cm and was filled with stainless steel wire gauze spirals. The reflux ratio at the top of the column was 1:10. Below 195° C., 439 g of product were obtained, 96.5% of this being the cis derivative. At 195°–198° C., 331 g of an intermediate fraction comprising 47.2% of the cis derivative and 52.7% of the trans derivative distilled over. trans-3-(4'-tert.-Butylcyclohex-1'-yl)-2-methyl-1-(N-di-n-propylamino)-propane then passed over at 198° C. The distillation was completed without the top of the column. 250 g of 99.8% pure product were obtained.

The yield was increased to 96.5% by using the intermediate fraction in the next distillation batches.

Because of the small difference in the boiling points of the cis and trans compounds, the distillation has to be monitored by gas chromatography.

C. Conversion to a salt

Fumaric acid was added to 29.5 g of the trans compound obtained as described in B.b), in 65 ml of hot ethanol. On cooling the mixture, 29 g of hydrogen fumarate of melting point 127°–132° C. crystallized out. The hydrobromide (m.p.=141°–147° C.), the hydriodide (m.p.=142°–146° C.) and the oxalate (m.p.=147° C.) were obtained in a similar manner.

The following compounds were prepared, or can be prepared, by a similar procedure:

2. trans-3-(4'-tert.-Butylcyclohex-1'-yl)-2-methyl-1-(N-ethyl-N-n-propylamino)-propane, bp.: 187° C./33 mbar
3. trans-3-[4'-(1'-Dimethyl-n-propyl)-cyclohex-1'-yl)]-2-methyl-1-(N-ethyl-N-n-propylamino)-propane.
4. trans-3-[4'-(1''-Methylcyclopent-1''-yl)-cyclohex-1'-yl)]-methyl-(N-di-n-propylamino)-propane.

Examples of pharmaceutical formulations

I Cream (a) Active compound (Example 1, A.b)): 0.5 g
(b) Glycerol monostearate: 10.0 g
(c) Cetyl alcohol: 5.0 g
(d) Polyethylene glycol-400 stearate: 10.0 g
(e) Polyethylene glycol sorbitan monostearate: 10.0 g
(f) Propylene glycol: 6.0 g
(g) Methyl p-hydroxybenzoate: 0.2 g
(h) Deionized water, to make up to 100.0 g The very finely powdered active compound is suspended in propylene glycol, and the suspension is stirred into a melt, at 65° C., comprising glycerol monostearate, cetyl alcohol, polyethylene glycol-400 stearate and polyethylene glycol soribtan monostearate. A solution, at 70° C., of methyl p-hydroxybenzoate in water is emulsified in this mixture, the emulsion is cooled, and the resulting cream is homogenized in a colloid mill and then introduced into tubes.

II Powder (a) Active compound (Example 1, C): 0.5 g
(b) Zinc oxide: 10.0 g
(c) Magnesium oxide: 10.0 g
(d) Finely divided silicon dioxide: 2.5 g
(e) Magnesium stearate: 1.0 g
(f) Talc: 75.5 g The active compound is micronized in a jet mill employing air, and is then mixed with the other components to give a homogeneous mixture. This is forced through a sieve of No. 7 mesh size and then introduced into polyethylene containers with a dusting attachment.

We claim:

1. A trans-3-(4'-tert.-butylcyclohex-1'-yl)-2-methyl-1-dialkylaminopropane of the formula I

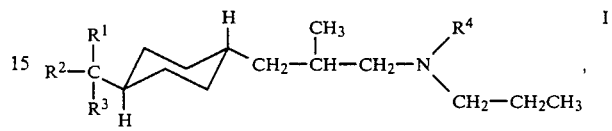

where $R^1$, $R^2$ and $R^3$ are identical or different and are each $C_1$-$C_4$-alkyl, or two of the radicals $R^1$, $R^2$ and $R^3$ together can form a cyclopentyl or cyclohexyl radical, and $R^4$ is ethyl or n-propyl, and its salts with physiologically tolerated acids.

2. trans-3-(4'-tert.-Butylcyclohex-1'-yl)-2-methyl-1-(N-di-n-propylamino)-propane.

3. trans-3-(4'-tert.-Butylcyclohex-1'-yl)-2-methyl-1-(N-ethyl-N-n-propylamino)-propane.

4. A therapeutic antimycotic composition comprising a pharmaceutical excipient and an effective amount of a compound of claim 1 as the active ingredient.

5. The method of treating dermatomycoses, dermatophytoses and generalized mycoses in a patient suffering therefrom, which comprises administering an effective amount of a compound of claim 1.

* * * * *